US006752764B2

(12) United States Patent
Oh

(10) Patent No.: US 6,752,764 B2
(45) Date of Patent: Jun. 22, 2004

(54) POCKET SPHYGMOMANOMETER

(76) Inventor: Man S. Oh, 138 Wheatley Rd., Old Westbury, NY (US) 11568

( * ) Notice: Subject to any disclaimer, the term of this patent is extended or adjusted under 35 U.S.C. 154(b) by 41 days.

(21) Appl. No.: 10/235,146

(22) Filed: Sep. 4, 2002

(65) Prior Publication Data
US 2004/0044289 A1 Mar. 4, 2004

(51) Int. Cl.$^7$ .................................. A61B 5/02
(52) U.S. Cl. ..................... 600/497; 600/498; 73/385
(58) Field of Search ................. 600/487, 486, 600/485, 481, 488, 490, 491, 497; 73/384, 385

(56) References Cited

U.S. PATENT DOCUMENTS

| 1,569,097 A | 1/1926 | MacKenzie |
| 1,830,829 A | 11/1931 | Eyster |
| 2,228,023 A | 1/1941 | Abbert |
| 2,437,861 A | 3/1948 | Rohr |
| 2,669,125 A | 2/1954 | Hesse |
| 3,056,299 A | 10/1962 | Körmendy |
| 4,942,879 A * | 7/1990 | Yokozuka ............... 600/497 |

* cited by examiner

Primary Examiner—Max F. Hindenburg
Assistant Examiner—Navin Natnithithadha
(74) Attorney, Agent, or Firm—Ostrolenk, Faber, Gerb & Soffen, LLP

(57) ABSTRACT

A sphygmomanometer with an air reservoir connected above a tube for a mercury column and a selectively openable and closeable valve to the air reservoir. With the valve open, first blood pressure measurements can be made by pressure rising in the mercury reservoir. With the valve closed, the air above the mercury column resists rise in the mercury column but also permits higher pressure measurements using the same mercury column. One scale at the mercury tube measures the pressure with the valve open and another scale at the tube measures the pressure with the valve closed. The measurements with the valve closed are calibrated by appropriately altering the volume of the air reservoir depending upon altitude at barometric pressure. The sphygmomanometer can be used to perform a mercury drop test for determining the altitude at which the sphygmomanometer is located.

20 Claims, 4 Drawing Sheets

Table 1: Changes in barometer with altitude:

| Altitude (Feet) | Barometric pressure (mmHg) |
|---:|---:|
| 0 | 760 |
| 500 | 746 |
| 1000 | 733 |
| 1500 | 720 |
| 2000 | 707 |
| 2500 | 694 |
| 3000 | 681 |
| 3500 | 669 |
| 4000 | 656 |
| 4500 | 644 |
| 5000 | 632 |
| 5500 | 620 |
| 6000 | 609 |
| 6500 | 598 |
| 7000 | 587 |
| 7500 | 576 |
| 8000 | 565 |
| 8500 | 554 |
| 9000 | 543 |
| 9500 | 533 |
| 10000 | 523 |

FIG. 2

Table 2  PREDICTED PRESSURE READINGS COMPARED WITH PRESSURE SCALE READINGS AT DIFFERENT ALTITUDE AFTER THE AIR RESERVOIR VOLUME IS REDUCED WITH PLACEMENT OF CHIPS INSIDE THE AIR RESERVOIR:

| Altitude (feet) | 0 | 500 | 1000 | 1500 | 2000 | 2500 | 3000 | 3500 | 4000 | 4500 | 5000 | 5500 | 6000 | 6500 | 7000 | 7500 | 8000 | 8500 | 9000 | 9500 | 10000 |
|---|---|---|---|---|---|---|---|---|---|---|---|---|---|---|---|---|---|---|---|---|---|
| Baromet P | 760 | 746 | 733 | 720 | 707 | 694 | 681 | 669 | 656 | 644 | 632 | 620 | 609 | 598 | 587 | 576 | 565 | 554 | 543 | 533 | 523 |
| # chips | 0 | 1 | 2 | 3 | 4 | 5 | 6 | 7 | 8 | 9 | 10 | 11 | 12 | 13 | 14 | 15 | 16 | 17 | 18 | 19 | 20 |
| P on Scale / Hg Ht | pred P | pred P | pred P | pred P | pred P | pred P | pred P | pred P | pred P | pred P | pred P | pred P | pred P | pred P | pred P | pred P | pred P | pred P | pred P | pred P | pred P |
| 300 / 6.46 | 300 | 300 | 300 | 300 | 299 | 299 | 299 | 299 | 299 | 298 | 299 | 299 | 299 | 300 | 300 | 300 | 300 | 301 | 301 | 302 | 302 |
| 290 / 6.26 | 290 | 290 | 290 | 290 | 290 | 289 | 289 | 289 | 289 | 289 | 289 | 289 | 289 | 290 | 290 | 290 | 290 | 291 | 291 | 291 | 292 |
| 280 / 6.05 | 280 | 280 | 280 | 279 | 279 | 279 | 279 | 279 | 279 | 279 | 279 | 279 | 279 | 279 | 279 | 280 | 280 | 280 | 280 | 281 | 281 |
| 270 / 5.85 | 270 | 270 | 270 | 270 | 269 | 269 | 269 | 269 | 269 | 269 | 269 | 269 | 269 | 269 | 270 | 270 | 270 | 270 | 270 | 271 | 271 |
| 260 / 5.64 | 260 | 260 | 260 | 259 | 259 | 259 | 259 | 259 | 259 | 259 | 259 | 259 | 259 | 259 | 259 | 259 | 260 | 260 | 260 | 260 | 261 |
| 250 / 5.44 | 250 | 250 | 250 | 250 | 250 | 249 | 249 | 249 | 249 | 249 | 249 | 249 | 249 | 249 | 249 | 250 | 250 | 250 | 250 | 250 | 251 |
| 240 / 5.23 | 240 | 240 | 240 | 240 | 239 | 239 | 239 | 239 | 239 | 239 | 239 | 239 | 239 | 239 | 239 | 239 | 239 | 240 | 240 | 240 | 240 |
| 230 / 5.02 | 230 | 230 | 230 | 229 | 229 | 229 | 229 | 229 | 229 | 229 | 229 | 229 | 229 | 229 | 229 | 229 | 229 | 229 | 230 | 230 | 230 |
| 220 / 4.81 | 220 | 220 | 220 | 219 | 219 | 219 | 219 | 219 | 219 | 219 | 219 | 219 | 219 | 219 | 219 | 219 | 219 | 219 | 219 | 220 | 220 |
| 210 / 4.6 | 210 | 210 | 210 | 209 | 209 | 209 | 209 | 209 | 209 | 209 | 209 | 209 | 209 | 209 | 209 | 209 | 209 | 209 | 209 | 209 | 210 |
| 200 / 4.39 | 200 | 200 | 200 | 199 | 199 | 199 | 199 | 199 | 199 | 199 | 199 | 199 | 199 | 199 | 199 | 199 | 199 | 199 | 199 | 199 | 200 |
| 190 / 4.18 | 190 | 190 | 190 | 190 | 189 | 189 | 189 | 189 | 189 | 189 | 189 | 189 | 189 | 189 | 189 | 189 | 189 | 189 | 189 | 189 | 190 |
| 180 / 3.97 | 180 | 180 | 180 | 180 | 180 | 179 | 179 | 179 | 179 | 179 | 179 | 179 | 179 | 179 | 179 | 179 | 179 | 179 | 179 | 179 | 180 |
| 170 / 3.75 | 170 | 170 | 170 | 170 | 169 | 169 | 169 | 169 | 169 | 169 | 169 | 169 | 169 | 169 | 169 | 169 | 169 | 169 | 169 | 169 | 169 |
| 160 / 3.54 | 160 | 160 | 160 | 160 | 159 | 159 | 159 | 159 | 159 | 159 | 159 | 159 | 159 | 159 | 159 | 159 | 159 | 159 | 159 | 159 | 159 |
| 150 / 3.32 | 150 | 150 | 149 | 149 | 149 | 149 | 149 | 149 | 149 | 149 | 149 | 149 | 149 | 149 | 149 | 149 | 149 | 149 | 149 | 149 | 149 |
| 140 / 3.11 | 140 | 140 | 140 | 140 | 140 | 139 | 139 | 139 | 139 | 139 | 139 | 139 | 139 | 139 | 139 | 139 | 139 | 139 | 139 | 139 | 139 |
| 130 / 2.89 | 130 | 130 | 130 | 130 | 129 | 129 | 129 | 129 | 129 | 129 | 129 | 129 | 129 | 129 | 129 | 129 | 129 | 129 | 129 | 129 | 129 |
| 120 / 2.67 | 120 | 120 | 120 | 119 | 119 | 119 | 119 | 119 | 119 | 119 | 119 | 119 | 119 | 119 | 119 | 119 | 119 | 119 | 119 | 119 | 119 |
| 110 / 2.45 | 110 | 110 | 109 | 109 | 109 | 109 | 109 | 109 | 109 | 109 | 109 | 109 | 109 | 109 | 109 | 109 | 109 | 109 | 109 | 109 | 109 |
| 100 / 2.23 | 100 | 100 | 99 | 99 | 99 | 99 | 99 | 99 | 99 | 99 | 99 | 99 | 99 | 99 | 99 | 99 | 99 | 99 | 99 | 99 | 99 |
| 90 / 2.01 | 90 | 90 | 89 | 89 | 89 | 89 | 89 | 89 | 89 | 89 | 89 | 89 | 89 | 89 | 89 | 89 | 89 | 89 | 89 | 89 | 89 |
| 80 / 1.79 | 80 | 80 | 80 | 80 | 80 | 80 | 80 | 79 | 79 | 79 | 79 | 79 | 79 | 79 | 79 | 79 | 79 | 79 | 79 | 79 | 79 |
| 70 / 1.57 | 70 | 70 | 70 | 70 | 69 | 69 | 69 | 69 | 69 | 69 | 69 | 69 | 69 | 69 | 69 | 69 | 69 | 69 | 69 | 69 | 69 |
| 60 / 1.35 | 60 | 60 | 60 | 60 | 60 | 60 | 59 | 59 | 59 | 59 | 59 | 59 | 59 | 59 | 59 | 59 | 59 | 59 | 59 | 59 | 59 |
| 50 / 1.13 | 50 | 50 | 50 | 50 | 50 | 50 | 50 | 50 | 50 | 50 | 50 | 49 | 49 | 49 | 49 | 49 | 49 | 49 | 49 | 49 | 49 |
| 40 / 0.9 | 40 | 40 | 40 | 40 | 40 | 40 | 40 | 39 | 39 | 39 | 39 | 39 | 39 | 39 | 39 | 39 | 39 | 39 | 39 | 39 | 39 |
| 30 / 0.68 | 30 | 30 | 30 | 30 | 30 | 30 | 30 | 30 | 30 | 30 | 30 | 30 | 30 | 30 | 30 | 30 | 30 | 30 | 30 | 30 | 30 |
| 20 / 0.45 | 20 | 20 | 20 | 20 | 20 | 20 | 20 | 20 | 20 | 20 | 20 | 20 | 20 | 20 | 20 | 20 | 20 | 20 | 20 | 20 | 20 |
| 10 / 0.23 | 10 | 10 | 10 | 10 | 10 | 10 | 10 | 10 | 10 | 10 | 10 | 10 | 10 | 10 | 10 | 10 | 10 | 10 | 10 | 10 | 10 |
| 0 / 0 | 0 | 0 | 0 | 0 | 0 | 0 | 0 | 0 | 0 | 0 | 0 | 0 | 0 | 0 | 0 | 0 | 0 | 0 | 0 | 0 | 0 |

FIG. 3

Hg Drop Test: A drop in P with a closed valve.

| Altitude | Sea Level | 1000' | 2000' | 3000' | 4000' | 5000' | 6000' | 7000' | 8000' | 9000' | 10000' |
|---|---|---|---|---|---|---|---|---|---|---|---|
| Hg level drop | 68 | 67.2 | 65.7 | 64.0 | 62.4 | 60.3 | 59.4 | 57.9 | 56.3 | 54.7 | 52.7 |
| Hg drop after correction of air reservoir volume | 68 | 68 | 68 | 68 | 67 | 67 | 67 | 67 | 67 | 67 | 67 |

FIG. 4

POCKET SPHYGMOMANOMETER

BACKGROUND OF THE INVENTION

The present invention relates to a mercury sphygmomanometer that is compact, easy to manufacture, and safe from mercury spillage.

A mercury sphygmomanometer is one of several blood pressure-measuring devices currently available. Other measuring devices include aneroid pressure measuring manometers and electronic manometers. Aneroid and electronic manometers tend to be smaller in size, lighter in weight, and more compact than mercury sphygmomanometers, but their accuracy is always in doubt. For most assured accuracy the standard among different blood pressure measuring devices is the mercury sphygmomanometer. The mercury sphygmomanometer measures arterial blood pressure and indicates its measurement by the height of a mercury column. The conventional mercury sphygmomanometer uses a transparent rigid plastic or glass tube through which a mercury column rises and falls during blood pressure measurement. In a typical mercury sphygmomanometer, the mercury tube is tall enough to allow the mercury column to reach a maximum height of 300 mm. Thus, the height of the mercury tube establishes the minimum height or length of the mercury sphygmomanometer when the device is stored or carried.

In order to obviate the size limitation of the conventional mercury sphygmomanometer and to allow a compact size for easy portability and storage, three approaches have been taken. One approach is to use a flexible tube for the mercury column, which could be folded during storage for compactness, e.g. as disclosed in U.S. Pat. No. 2,603,210. Another approach is to provide an articulation or a hinge located part way along the tube and to fold and unfold the mercury tube at the articulation or hinge for storage and usage of the device, e.g. as disclosed in U.S. Pat. Nos. 1,093,199 and 1,077,365. In another approach using a hinge mechanism, as described in U.S. Pat. No. 1,474,853, the mercury column used for blood pressure reading is a single tube. But this device requires a third tube to act as a mercury reservoir which is placed between a tube for the mercury column used for blood pressure readings and another tube connected to the air inflation cuff.

Repeated folding of a flexible tube can damage the tube and cause mercury spillage. Use of a hinge or an articulation would add complexity and cost to the manufacturing process in order to minimize risk of mercury spillage along the hinge or the articulation.

The third type of device is based on reducing the height of the mercury column based on Boyle's Law, which states: if the volume of a gas and its temperature are kept constant, the pressure of the gas is inversely proportionate to its volume. Unlike a conventional mercury sphygmomanometer with a mercury tube in communication with an outside air, the mercury tube in this device is in a closed system. It is in communication with an air reservoir having a fixed volume through a passageway containing a filter, which allows air to pass through the filter between the two compartments, but blocks mercury from entering the reservoir.

Because the air valve that connects the air reservoir to the outside air is closed, pressure develops in the air reservoir as well as in the air compartment above the mercury column. This air pressure will be exerted on the rising mercury column. Hence, the pressure at the bottom of the mercury column is equal to the air pressure on the top of the mercury column plus the pressure generated by the weight of mercury, which is proportionate to the height of the mercury column. The maximum height of mercury column needed to obtain a certain maximal pressure measurement (e.g. 300 mmHg) can be reduced to a length that is much shorter than 300 mmHg. This feature allows easy portability of the device.

The present invention enables the measurement of blood pressure using a variation of the third principle described above. The invention involves blood pressure measurements using two separate scales that are displayed along the mercury column, e.g. at opposite sides of the column or at one side. One scale, e.g. along one side of the mercury column, represents blood pressure measurements made with the air valve open. The other scale, e.g. along the other side of the mercury column, represents the pressure measurements with the air valve closed. The maximum blood pressure scale with the open air valve is dictated by the desired maximal blood pressure readings. For example, if a maximal blood pressure reading of 180 mmHg is desired, the required height of the mercury column would be 7.086 inches (180/25.4=7.086). If a maximal pressure reading of 200 mmHg is desired, the required maximal height would be 7.874 inches). In either example, the overall length of the device would be considerably shorter than the conventional mercury sphygmomanometer.

The advantage of the dual scale system (one scale, e.g. on one side with a closed air valve, and the other scale, e.g. on the other side with an open air valve) is in the easy readability of the blood pressure scales. When blood pressure is measured entirely with the air valve closed (as claimed by the U.S. Pat. No. xx), the advantage in compactness is counterbalanced by reduced readability of the blood pressure scales. In a conventional mercury sphygomomanometer, the blood pressure scales are depicted alongside the mercury column at intervals of about 2 mm in length. If the device were to be created using the principles claimed by U.S. Pat. No. xxx, the blood pressure scales would have to be depicted at shorter intervals than 2 mm. For example, if the overall length of the mercury column were to be reduced from 300 mmHg to 180 mmHg (reduced to 60%), the actual distance of each 2 mm scale would be only 1.2 mm (reduced to 60%). In the device to be produced using the principle claimed by the present invention, the actual distance of the blood pressure scales with the open air valve would be the same as that of the conventional device. With the open air valve, no additional pressure is exerted on the mercury column, and the pressure at the bottom of the mercury column depends solely on the height of the mercury column. Normotensive subjects and most hypertensive subjects with adequate blood pressure control will only need to use the scale with the open-valve system if the maximal pressure of such device is 180 mmHg. The pressure readings using the device with the open air valve would be as accurate and easy as using the conventional mercury manometer, since the scale of pressure readings are the same as those of a conventional mercury manometer.

When the blood pressure to be measured is higher than the maximal reading possible with the open air valve, measurement would then be repeated with the closed air valve. However, pressure readings made with a closed air valve would not be as accurate as those made with the open air valve for two reasons. 1) The air pressure that develops on the top of the mercury column may vary with variations in the atmospheric pressure. 2) Cramming of the displayed pressure scales into a shorter height space makes it harder to read the scales. However, A slight error in readings with the closed air valve is clinically unimportant, because the closed air valve scale would be used only when the pressure is higher than the maximal readings possible with the open air valve scale; when the pressure is lower, the open air valve scale is used. For example, a distinction between a pressure difference of 85 and 90 mmHg would be more important while the distinction between 250 and 255 mmHg is likely less important.

A second feature of the present invention relates to minimizing errors in pressure measurement resulting from variation in atmospheric pressure due primarily to a change in the altitude at which the measurement is made. When blood pressure is measured using the closed air valve, the air in the mercury tube above the mercury column is compressed within a closed system that communicates with the air reservoir when the mercury column rises. The rise in pressure in the air reservoir system during a blood pressure measurement depends on the magnitude of the reduction in the air space caused by a rising mercury column in relation to its overall original size. Another important fact is the original pressure in the air reservoir, which is equal to the atmospheric pressure where the device is used. For example, if the device is used at a sea level, reduction in air space volume from 7.33 ml to 6.33 ml, would increase the pressure to 880 mmHg (an increase of 120 mmHg) as shown in the following equation: $760 \times 7.33 = 880 \times 6.33$.

Barometric pressure is not constant, but a daily variation in any given area is usually less than 5 mmHg. Over the past 150 years, the maximal variation in pressure was shown to be about 15 mmHg. This magnitude of variations in atmospheric pressure would have little effect on the overall blood pressure calculation. An error in blood pressure reading at 100 mmHg level with the variation in atmospheric pressure by 5 mmHg, would be less than 1 mmHg.

Much larger changes in the atmospheric pressure occur with a change in altitude than with a change in weather. For example the atmospheric pressure at an altitude of 5,000 feet (Denver, Colo.) is about 632 mmHg (a reduction of 128 mmHg). See Table 1 which appears as FIG. 2 hereof.

A blood pressure measurement based on an assumed atmospheric pressure of 760 mmHg in an area with an actual atmospheric pressure of 632 mmHg would result in a substantial error in the blood pressure measurement. For example, if the same device as above were used with the air valve closed at an altitude of 5,000 feet (632 mmHg of atmospheric pressure), a reduction in air space volume from 7.33 to 6.33 ml would increase the pressure from 632 to 732 mmHg (increase of only 100 mmHg). To minimize an error caused by variations in atmospheric pressure due to changes in altitude, solid chips of known volume may be placed into the air reservoir chamber or another device may be attached or placed in the air reservoir which can be manually adjusted to vary the volume of air in the air reservoir. This can be achieved by reducing the air reservoir volume. Table 2 which appears as FIG. 3 hereof shows a sample calculation for the number of chips of one size that might be added to adjust air reservoir volume at different altitudes in order to compensate for reduced atmospheric pressure. With these adjustments, the error in pressure readings may be 2 mmHg or less at an altitude of 10,000 feet. At lower altitudes, errors are much lower. These magnitudes of errors are clinically insignificant, especially because the errors may occur only in a closed system which is used only when blood pressure value is very high. Changes in the volume of the air reservoir can be made when the user of the device moves to a different location. The information on altitude of different cities or localities could be shown in the instruction manual of the device along with instructions on compensating a closed system.

In a third aspect of the present invention, a mechanism is provided that measures the atmospheric pressure (and therefore the altitude indirectly) of the location where the device is being used. This would be accomplished by creating a mark (or marks) alongside the blood pressure scale that would coincide with the mercury drop level during the mercury drop test described below.

Mercury drop test: Fill the mercury tube to the top with mercury by tilting the device while the air reservoir valve is open. (There should be no air bubble in the mercury column during this procedure). When the mercury column reaches the top of the mercury tube, it will not advance any further because the top is blocked by a filter that allows air passage, but not mercury passage. At this point, close the air valve, and then let the device stand in its normal position. As the mercury level falls under the force of gravity, a negative pressure develops in the air reservoir because the falling mercury level creates additional space above the mercury column. When the negative pressure in the air reservoir equals the pressure generated by the height of the mercury column, the mercury level stops falling.

The amount of negative pressure that develops with the falling mercury level during the mercury drop test depends on the baseline air pressure of the reservoir, which is equal to the atmospheric pressure when the air valve is open. At sea level (an atmospheric pressure of 760 mmHg), the mercury level drop can be calculated using the following formula:

$760 \times 6.33 = P \times (6.33 + A/180)$, where P is the new pressure inside the air chamber after the mercury drop (which is subatmospheric pressure), 760 is the atmospheric pressure at the sea level, and A the mercury level at the top of the mercury column depicted on the scale of 0 to 180.

The difference between 760 and P is the magnitude of negative pressure in the air reservoir, and this would be equal to the A. A calculation using the above formula at sea level indicates that mercury would drop to the level of 68 mmHg during the mercury drop test. If the same test were performed at an altitude of 5,000 feet (the atmospheric pressure of 632 mmHg), the mercury level during the drop test would produce a level of 60.3 mmHg. The drop is greater because the magnitude of negative air pressure that develops in the air reservoir by the mercury drop would be less because of the lower baseline atmospheric pressure. The depiction of such a scale alongside the mercury column can be used to determine the atmospheric pressure and altitude of the place where the device is used. When the mercury drop test is repeated after reduction of the air reservoir volume e.g. by addition of an appropriate number of chips, the mercury level would drop to the level similar (67 mmHg) to that at sea level.

Table 3 appears as FIG. 4 hereof and shows the mercury level drop at various altitudes and the drop after correction of air reservoir volume.

BRIEF DESCRIPTION OF THE DRAWING FIGURES

FIG. 2 is a Table 1 which shows changes in atmospheric pressure with changes in altitude.

FIG. 3 is a Table 2 which shows adjustments in air reservoir volume to compensate for altitude changes; and FIG. 4 is Table 3 which shows a mercury level drop at various altitudes and after correction of air reservoir volumes.

DESCRIPTION OF PREFERRED EMBODIMENT

Figure 1:
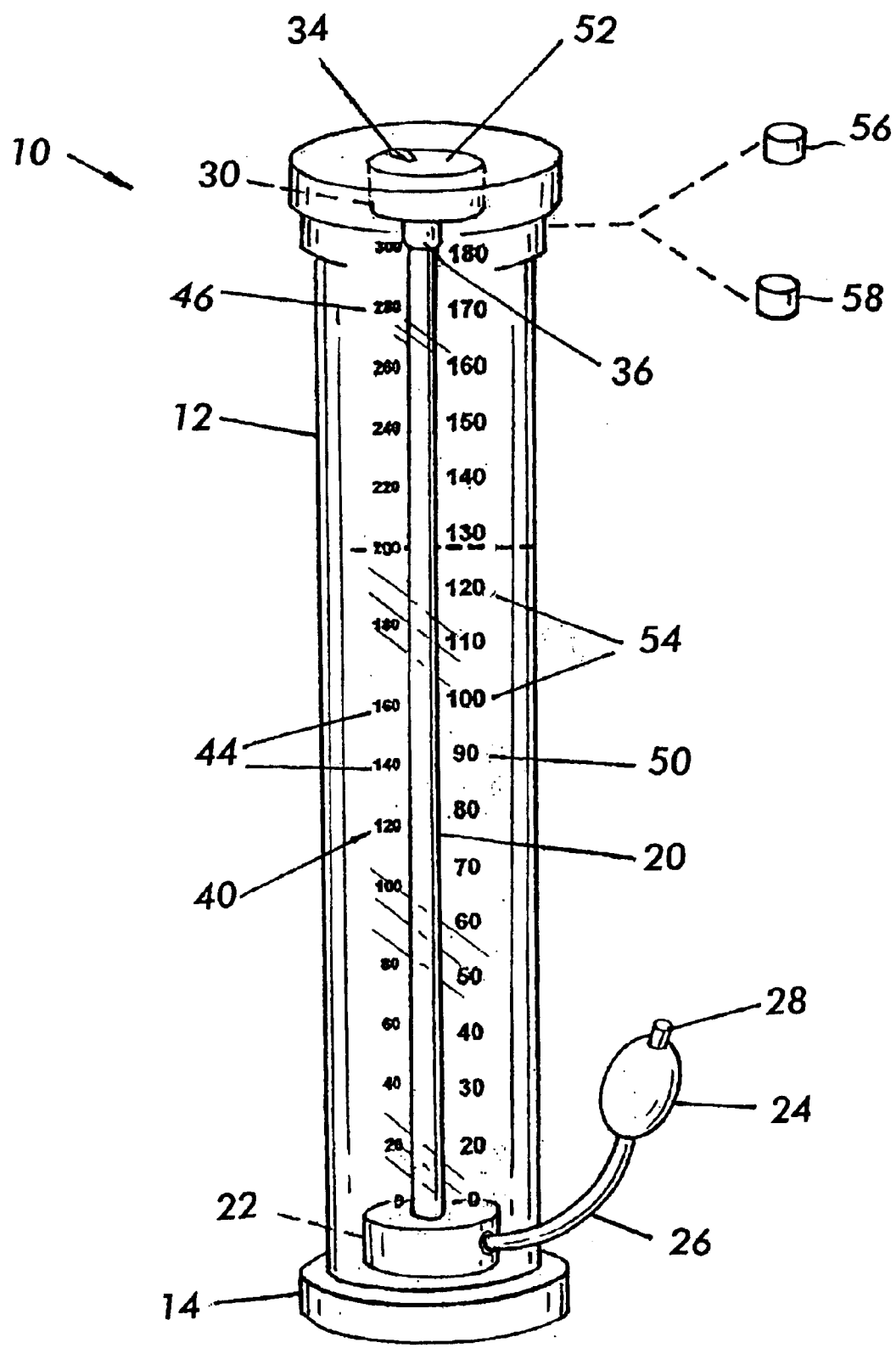
FIG. 1 is a front view of an example of sphygmomanometer according to the invention including various features of the invention.

FIG. 1 shows schematically a sphygmomanometer according to the present invention. A sphygmomanometer 10 includes a body 12 which is stood upright on its stand 14 so that the body supports a tube 20 upright when the sphygmomanometer is to be used. The tube 20 defines a column for containing mercury. A reservoir 22 below the tube 20 holds a supply of liquid mercury which is to be raised through the tube to define a mercury column. A standard air pressure pump, here a bulb 24 may be manually operated to supply air pressure through the tube 26 to the reservoir 22. The air pressure raises mercury out of the reservoir into the tube 20 defining a mercury column. A standard release valve 28 at the air pressure supply for communicating anywhere up to the reservoir 22 enables release of the air pressure built up and permits return of the mercury from the tube 20 into the reservoir 22. The tube 20 is at the outside of the body 12 or at least visible through the side of the body 12 since the height of the mercury column in the tube 20 is determinative of the blood pressure being measured.

An air reservoir 30, illustrated as being in the body 12, communicates with the upper end of the tube 20, so that the tube 20 and the reservoir 30 together define an air chamber. The volume of the air reservoir 30 is known and, coupled with the volume of the column 20 before the mercury reservoir is pressurized, the air volume in the air chamber comprised of the air reservoir 30 and the tube 20 is a known value.

In the preferred form of the sphygmomanometer, there is an air release valve 34 connected into the reservoir 30. When the valve is open, the tube 20 and reservoir 30 communicate to the outside and the air pressure in the tube 20 above the mercury column and in the reservoir 30 is at atmospheric pressure as the air column rises and falls. With the valve 34 open, the sphygmomanometer is like a conventional sphygmomanometer in that the air space above the mercury column communicates with the outside.

In order to retain the mercury and prevent it from escaping from the tube 20, there is a standard filter 36 between the tube 20 and the air reservoir 30, the filter being porous to permit the free passage of air through the filter while being sufficiently fine to keep the liquid mercury in the tube 20 and prevent its escape no matter how the body 12 may be oriented in use or in storage or under any expected pressure conditions to which the mercury in the tube 20 might be exposed.

When the valve 34 is operated to the closed condition, air in the air chamber comprised of the reservoir 30 and the volume in the tube 20 above the mercury column in the tube 20 cannot escape as the mercury column rises. As the mercury column rises, the air pressure increases above the mercury column, and the rise of the mercury column is resisted. As a result, the increase in pressure in the mercury reservoir 22 raises the mercury column to a shorter extent than would be the case if the valve 34 were open and the reservoir 30 communicates to the outside. The influence of Boyle's Law on the volume of air in the tube and the air reservoir and on the pressure exerted against arising of the mercury column has been fully described above.

On the body 12 adjacent to the tube 20 there are two measuring scales for measuring the height of the mercury column. For simplicity the scales are on opposite sides of the tube, but the scales may be on the same side of the tube or otherwise placed for purposes of indicating the height of the mercury column. The first scale 40 measures the height of the mercury column when the valve 34 is open. Assuming, for example, that each of the scale markings indicates increments of a certain number of millimeters of mercury column e.g. 2 millimeters, the gradations 44 of the scale 40 are relatively more widely spaced apart, since there is no air pressure build up above the column of mercury in the tube 20. When the pressure in the reservoir 22 has been raised sufficiently, the column of mercury will have been raised up to the filter 36 and cannot rise any further. Pressure measurements for pressures below the height of the mercury column at the filter 36 can be accurately taken. But any pressure measurements for a mercury column higher than the topmost gradation 46 on the scale 40 cannot be taken.

For that purpose, the second scale 50 is operative. After all of the mercury in the tube 20 has been permitted to descend into the reservoir 22 with the valve 34 open, the valve 34 is closed and the reservoir 22 is pressurized. Now the rising column of mercury increases the pressure of the chamber of air in the tube 20 above the mercury column and in the air reservoir 30. The downward pressure on the mercury column does not prevent the column rising as the mercury reservoir is increasingly pressurized. But the downward pressure reduces the distance along the tube that the mercury column rises for each increment of pressure. The second scale 50 therefore has scale markings 54 which could indicate different pressure gradations, as illustrated, or the same pressure gradations as the markings 44 of the scale 40, but which would then be closer together. The scale 50 could not longer provide measurements of the actual rise in mercury column measured in millimeters. Rather, the scale is adjusted to take Boyle's law into account, so that the gradations would be closer together than the actual millimeter height levels, but the scale is calibrated to provide readings along the height of the tube in millimeter numbers that would correspond to millimeter readings of the actual column of mercury if the valve 34 were not closed. Using Boyle's law and the formulas described above, the scale markings 54 can be accurately placed on the body 12. Whereas the height of the first scale 40 with the valve 34 open limits the maximum pressure that can be developed in the mercury reservoir 22 and, for example, has the upper gradation 46 at a pressure level of only 180° of Hg, and since some blood pressure measurements well exceed 180° of Hg, and since the usual scaling in a sphygmomanometer may go up to 300 mm of Hg, for any measurement above the pressure level at the upper scale marking 46, a reading on the scale 50 with the valve 34 closed could be made up to a considerably higher level, e.g. 300 mm of Hg.

Therefore, the combination including the air chamber above the mercury column in the tube 20, coupled with the selectively openable and closeable valve 34 and the two scales 40 and 50 on the body 12 enables the full range of possible blood measurements now available on a larger size sphygmomanometer to be available on a shorter height sphygmomanometer, with the lower pressure measurements being taken on one scale (or on both scales if the user so desires), but with the higher pressure measurements being taken only on the second scales.

With the valve 34 to the reservoir 30 closed, the pressure system from the mercury reservoir 22 through the tube 20 and the reservoir 30 is a closed air pressure system and the change in the outside or atmospheric air pressure will cause a corresponding change on the air pressure in the reservoir 30 and in the air in the tube 20 above the mercury column. As barometric pressure decreases, particularly with an increase in altitude, when the valve 34 is opened, there is less volume of air in the reservoir and in the tube than at a lower altitude due to lower air density. That has an effect on the rise in the mercury column when the valve 34 is closed. As discussed above, there should be an adjustment of the column of the air space above the mercury column in the tube with the valve 34 closed in order to provide an accurate reading of the height of the mercury column with the valve 34 closed. One way to accomplish that is to appropriately vary the size of the air space above the mercury column to take into account the change in barometric pressure due to altitude change into account. To this end, the reservoir 30 may be opened by the lid 52 thereof being temporarily detachable to provide access into its interior. Various pieces or chips 56, 58 of selected volume are either provided separately from the body 10 or are included within the body and with the lid 52 removed, an appropriately sized chip or piece 56 and/or 58 is placed into the reservoir 30 to adjust the volume of the air space above the mercury column for the particular expected barometric pressure where the sphygmomanometer is to be used, e.g. a particular altitude. Either chips of varying size may be used or chips of one size my be used. Selection of the appropriate size chip or of the appropriate number of chips will correct adapt the volume of the air reservoir. Table 2 shows blood pressure scales at sea level when the air reservoir valve are closed, and blood pressure scales at higher altitudes with reduction of air reservoir volume with addition of chips to the air reservoir. The calculation also shows the actual pressure readings that are expected with corrected volumes in relation to the inscribed pressure scale.

Once that adjustment of the volume of the air reservoir is done, Boyle's law works to assure that the pressure level measured by the rise in the mercury column with the closed air reservoir will provide an accurate reading of the effective height of the mercury column at a particular blood pressure measurement.

The sphygmomanometer may be supplied with a necessary plurality of the chips 56, 58 for the altitudes of major areas, such as major cities or by a certain number of meters above sea level and the user simply installs the appropriate chip in the reservoir for the selected altitude and/or location where the the sphygmomanometer will thereafter be used.

In addition, the sphygmomanometer apparatus may be used to make an altitude determination using the mercury drop test, as described above.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A sphygmomanometer comprising:
 a body having a tube therein for holding and guiding a column of mercury; the tube having a bottom and a top;
 an air reservoir communicating with the top of the tube;
  an air valve communicating between the air reservoir and the outside for permitting the air reservoir to adopt outside pressure, and the valve being closeable to prevent entrance or exit of air in the reservoir and the tube;
 a mercury reservoir communicating with the tube for supplying mercury that rises in the tube dependent upon pressure applied in the mercury reservoir;
 a pressure connection to the mercury reservoir for supplying pressure to drive mercury up the tube;
 a first measuring scale at the tube and the body for indicating the height of the mercury column in the tube when the valve is open, and a second measuring scale at the tube and the body for indicating the height of the mercury column in the tube when the valve is closed.

2. The sphygmomanometer of claim 1, wherein the first and second scales are on the body adjacent to the tube.

3. The sphygmomanometer of claim 2, wherein the scales are on the body along opposite sides of the tube.

4. The sphygmomanometer of claim 3, wherein the tube is visible in the body and the scales are visible.

5. The sphygmomanometer of claim 1, further comprising a filter between the tube and the air reservoir enabling passage of air into and out of the tube and blocking passage of mercury.

6. The sphygmomanometer of claim 1, further comprising an air pressure supply device connected to the pressure connection and including therein a release valve operable for releasing pressure applied to the mercury reservoir.

7. The sphygmomanometer of claim 1, further comprising an adjusting device at the body for adjusting the volume of the air reservoir and thereby adjusting a volume ratio between the mercury column and the air reservoir.

8. The sphygmomanometer of claim 7, wherein the adjusting device comprises at least one piece selectively within the air reservoir to reduce the volume thereof and removable from the air reservoir.

9. A sphygmomanometer comprising:
 a body having a tube therein for holding and guiding a column of mercury; the tube having a bottom and a top;
 an air reservoir communicating with the top of the tube, the reservoir being closed to prevent entrance or exit of air in the reservoir and the tube;
 a mercury reservoir communicating with the tube for supplying mercury that rises in the tube dependent upon pressure applied in the mercury reservoir;
 a pressure connection to the mercury reservoir for supplying pressure to drive mercury up the tube;
 a measuring scale at the tube and the body for indicating the height of the mercury column in the tube and;
 an adjusting device at the body for adjusting the volume of the air reservoir and thereby adjusting a volume ratio between the mercury column and the air reservoir.

10. The sphygmomanometer of claim 9, further comprising an air pressure supply device connected to the pressure connection and including therein a release valve operable for releasing pressure applied to the mercury reservoir.

11. The sphygmomanometer of claim 9, wherein the adjusting device comprises at least one piece selectively within the air reservoir to reduce the volume thereof and removable from the air reservoir.

12. A method of measuring blood pressure, using a sphygmomanometer comprising:
 a body having a tube therein for holding and guiding a column of mercury; the tube having a bottom and a top;
 an air reservoir communicating with the top of the tube;
  an air valve communicating between the air reservoir and the outside for permitting the air reservoir to adopt outside pressure, and the valve being closeable to prevent entrance or exit of air in the reservoir and the tube;
 a mercury reservoir communicating with the tube for supplying mercury that rises in the tube dependent upon pressure applied in the mercury reservoir;

a pressure connection to the mercury reservoir for supplying pressure to drive mercury up the tube;

a first measuring scale at the tube and the body for indicating the height of the mercury column in the tube when the valve is open, and a second measuring scale at the tube and the body for indicating the height of the mercury column in the tube when the valve is closed;

the method comprising:

selectively opening the valve for measuring blood pressures up to a first level of mercury column, or selectively closing the valve and preventing exit of air from the air reservoir for measuring blood pressures up to a second level of mercury column, higher than the first level; and then supplying pressure to the pressure connection for raising mercury in the tube.

13. The method of claim 12, further comprising adjusting the volume of the air reservoir dependent upon barometric pressure in a manner such that the same pressure applied to the mercury reservoir will indicate the same second level of mercury column on the second scale regardless of the barometric pressure.

14. The method of claim 13, wherein the adjustment for barometric pressure is calibrated for adjusting for the altitude.

15. The method of claim 13, wherein the volume adjustment comprises inserting pieces of selected volumes in the air reservoir for adjusting the volume of the air reservoir in a selected manner.

16. A method of measuring blood pressure, using a sphygmomanometer comprising a body having a tube therein for holding and guiding a column of mercury; the tube having a bottom and a top;

an air reservoir communicating with the top of the tube; the reservoir being closed to prevent entrance or exit of air in the reservoir and the tube;

a mercury reservoir communicating with the tube for supplying mercury that rises in the tube dependent upon pressure applied in the mercury reservoir;

a pressure connection to the mercury reservoir for supplying pressure to drive mercury up the tube;

a measuring scale at the tube and the body for indicating the height of the mercury column in the tube;

the method comprising:

adjusting the volume of the air reservoir dependent upon barometric pressure in a manner such that the same pressure applied to the mercury reservoir will indicate the same level of mercury column on the scale regardless of the barometric pressure; and then supplying pressure to the pressure connection for raising mercury in the tube.

17. The method of claim 16, wherein the adjustment for barometric pressure is calibrated for adjusting for the altitude.

18. The method of claim 16, wherein the volume adjustment comprises inserting pieces of selected volumes in the air reservoir for adjusting the volume of the air reservoir in a selected manner.

19. A method of determining altitude by using a mercury sphygmomanometer, wherein the sphygmomanometer comprises:

a body having a tube therein for holding and guiding a column of mercury; the tube having a bottom and a top;

an air reservoir communicating with the top of the tube; a valve communicating between the air reservoir and the outside for permitting the air reservoir to adopt the outside pressure, and the valve being closeable to prevent entrance or exit of air in the reservoir and the tube;

a mercury reservoir communicating with the tube for supplying the mercury that rises in the tube dependent upon pressure applied in the mercury reservoir;

an air pressure connection to the mercury reservoir for supplying air under pressure to drive mercury up the tube;

an air pressure connection to the mercury reservoir for supplying air under pressure to drive mercury up the tube;

a measuring scale at the tube and the body for indicating the height of the mercury column in the tube;

the method comprising:

with the air valve open, filling the mercury tube to the top by tilting the body and the tube;

when the mercury column reaches the top of the tube, retaining the mercury in the tube, closing the air valve, orienting the sphygmomanometer so that the tube is in a normal vertical orientation, permitting the mercury level in the tube to fall under gravitational force for developing a negative pressure in the air reservoir, until the negative pressure in the air reservoir equals the pressure generated by the height of the mercury column and the mercury level stops falling; and calculating the altitude from a measure of the level to which the mercury column has fallen in the tube.

20. The method of claim 19, further comprising altering the volume of the air reservoir to adjust the level of the mercury column in the tube to compensate for pressure differences due to altitude differences.

* * * * *